US010587224B2

(12) United States Patent
Hekmatshoartabari et al.

(10) Patent No.: US 10,587,224 B2
(45) Date of Patent: Mar. 10, 2020

(54) LOW-POWER MULTI-STAGE AMPLIFIER FOR CAPACITIVE READING OF LOW-AMPLITUDE AND LOW-FREQUENCY SIGNALS

(71) Applicant: International Business Machines Corporation, Armonk, NY (US)

(72) Inventors: Bahman Hekmatshoartabari, White Plains, NY (US); Ghavam G. Shahidi, Pound Ridge, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/858,062

(22) Filed: Dec. 29, 2017

(65) Prior Publication Data

US 2019/0207559 A1   Jul. 4, 2019

(51) Int. Cl.
| H03F 3/04 | (2006.01) |
| H03F 1/02 | (2006.01) |
| H03F 3/187 | (2006.01) |
| A61B 5/00 | (2006.01) |
| A61B 5/0428 | (2006.01) |
| H01L 29/10 | (2006.01) |
| H01L 29/80 | (2006.01) |
| H01L 29/06 | (2006.01) |
| A61B 5/0496 | (2006.01) |
| A61B 5/0476 | (2006.01) |

(52) U.S. Cl.
CPC ......... *H03F 1/0205* (2013.01); *A61B 5/0428* (2013.01); *A61B 5/7225* (2013.01); *H03F 3/187* (2013.01); *A61B 5/0476* (2013.01); *A61B 5/0496* (2013.01); *H01L 29/0684* (2013.01); *H01L 29/1029* (2013.01); *H01L 29/802* (2013.01)

(58) Field of Classification Search
CPC ...... H03F 1/0205; H03F 3/187; A61B 5/7225
USPC .................. 330/296, 310, 98, 133, 150, 297
See application file for complete search history.

(56) References Cited

U.S. PATENT DOCUMENTS

| 6,949,979 B2* | 9/2005 | Lu ............................. H03F 1/22 330/305 |
| 7,336,123 B2 | 2/2008 | Yoshida et al. |
| 8,766,719 B2* | 7/2014 | Lai ......................... H03F 3/2176 330/129 |
| 9,093,548 B2 | 7/2015 | Hekmatshoar-Tabari et al. |
| 9,608,580 B2 | 3/2017 | Ko et al. |
| 9,748,281 B1 | 8/2017 | Hekmatshoartabari et al. |
| 2010/0033240 A1 | 2/2010 | Denison et al. |
| 2017/0229588 A1 | 8/2017 | Hekmatshoartabari et al. |

* cited by examiner

*Primary Examiner* — Khanh V Nguyen
*Assistant Examiner* — Khiem D Nguyen
(74) *Attorney, Agent, or Firm* — Ryan, Mason & Lewis, LLP

(57) ABSTRACT

Low-power multi-stage amplifiers are provided for capacitive reading of low-amplitude and low-frequency signals. An exemplary multi-stage amplifier comprises a plurality of amplification stages, wherein each of the amplification stages comprises an amplifying transistor and an active load, wherein substantially all of the amplification stages have one or more of an increasing DC bias level and a decreasing DC bias level relative to a prior stage, and wherein an output of a given one of the amplification stages is directly applied as an input to a subsequent one of the amplification stages.

20 Claims, 6 Drawing Sheets

LOW-POWER MULTI-STAGE AMPLIFIER FOR CAPACITIVE READING OF LOW-AMPLITUDE AND LOW-FREQUENCY SIGNALS

FIELD

The present disclosure relates to multi-stage amplifier circuits and methods.

BACKGROUND

Non-invasive reading of bio-electric signals from the body is inherently challenging because the signals are often weak and much of the information is often at low frequencies. As a result, high-gain and low-noise amplifiers are required. However, traditional capacitive DC blocking cannot be used between amplifier stages because the series capacitors block substantial low-frequency information unless the series capacitors are prohibitively large.

Furthermore, for ultra-low power applications, the power consumption required for high gain amplifiers can be prohibitively large. The reading of bio-electric signals is even more challenging in large-area and flexible electronics because thin-film transistors (TFTs) have lower performance than VLSI transistors and complementary (e.g., both n-channel and p-channel) TFTs are typically not available or feasible.

A need therefore exists for improved amplifiers for capacitive reading of low-amplitude and low-frequency signals.

SUMMARY

Embodiments of the disclosure provide low-power multi-stage amplifiers for capacitive reading of low-amplitude and low-frequency signals.

In one embodiment, an exemplary multi-stage amplifier comprises a plurality of amplification stages, wherein each of the amplification stages comprises an amplifying transistor and an active load, wherein substantially all of the amplification stages have one or more of an increasing DC bias level and a decreasing DC bias level relative to a prior stage, and wherein an output of a given one of the amplification stages is directly applied as an input to a subsequent one of the amplification stages.

In another embodiment, a method for amplifying a signal, comprises obtaining the signal; and applying the signal to a multi-stage amplifier, wherein the multi-stage amplifier comprises a plurality of amplification stages, wherein each of the amplification stages comprises an amplifying transistor and an active load, wherein each of the amplification stages has one or more of an increasing DC bias level and a decreasing DC bias level relative to a prior stage, and wherein an output of a given one of the amplification stages is directly applied as an input to a subsequent one of the amplification stages.

These and other objects, features and advantages of the present disclosure will become apparent from the following detailed description of illustrative embodiments thereof, which is to be read in connection with the accompanying drawings.

DETAILED DESCRIPTION

Illustrative embodiments of the disclosure may be described herein in the context of illustrative low-power multi-stage amplifiers for capacitive reading of low-amplitude and low-frequency signals. However, it is to be understood that embodiments of the disclosure are not limited to the illustrative low-power multi-stage amplifiers but instead are more broadly applicable to other suitable devices.

In one or more embodiments, a multi-stage low-power high-gain amplifier is provided, comprised of, for example, a plurality of thin-film heterojunction field effect transistors (HJFETs), a multi-level voltage bias and substantially no capacitive DC blocking between the amplifier stages. In some embodiments, the HJFETs are biased in the sub-threshold regime and have pinch-off voltages that are substantially zero.

While one or more illustrative embodiments employ heterojunction field effect transistors, other transistor types, such as metal oxide semiconductor field effect transistors (MOSFETs), may be employed, as would be apparent to a person of ordinary skill in the art.

As discussed above, non-invasive reading of bio-electric signals from the body is inherently challenging because the signals are often weak and much of the information is often at low frequencies. For example, an Electroencephalogram (EEG) that measures brain activity would be measuring signals in the range of 1~50 µV. Similarly, an electrooculogram (EOG) that measures eye activity would be measuring signals in the range of 1~50 mV. Electrocardiograms (ECGs) that measure heart activity would be measuring signals in the range of 10~100 mV (fetal ECGs may be as low as 1~10 µV), while electrogastrograms (EGGs) that measure stomach activity would be measuring signals in the range of 1~10 mV, and electromyograms (EMGs) that measure muscle activity would be measuring signals in the range of 10~100 mV.

Figure 1:
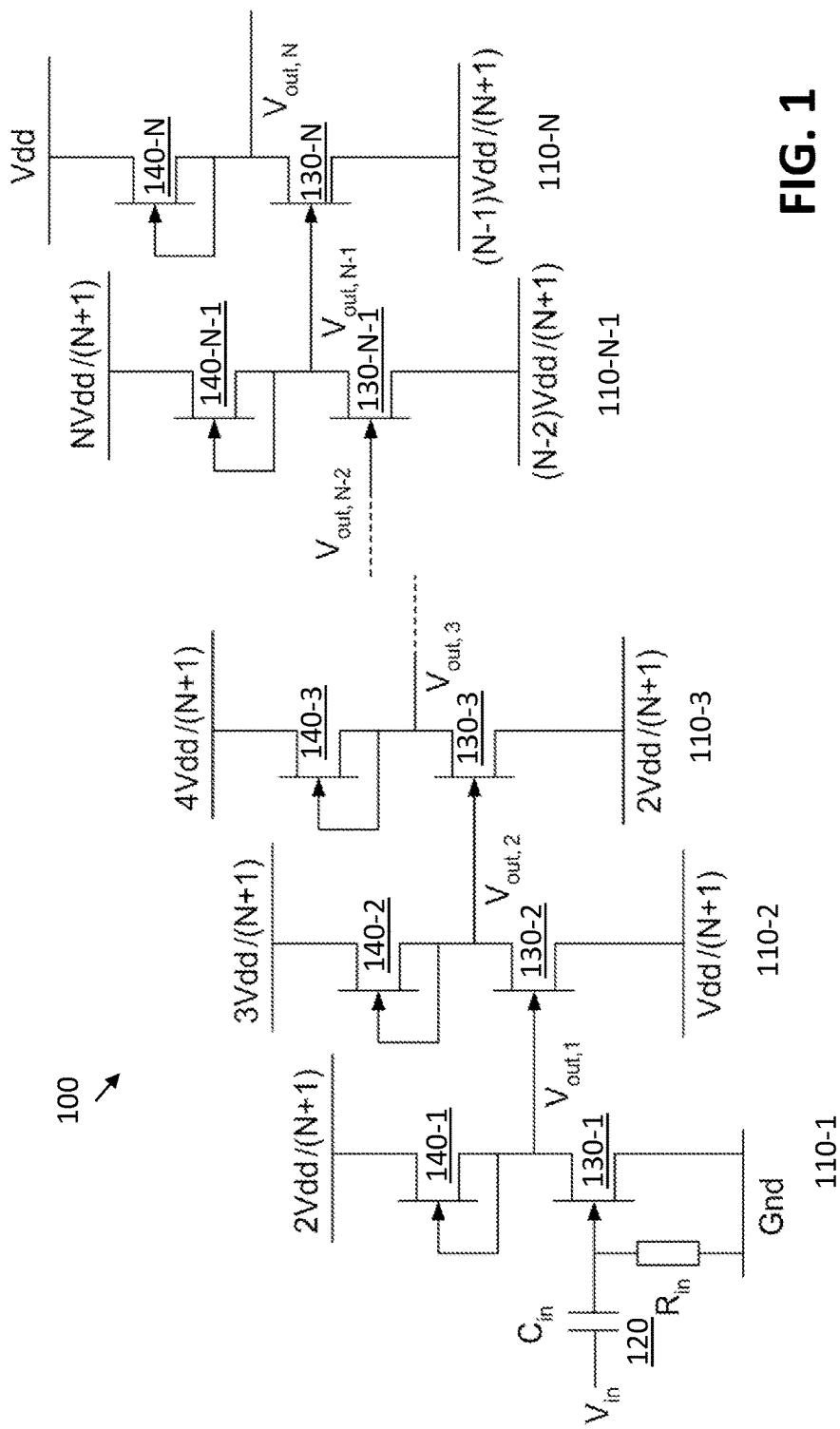
FIG. 1 depicts a multi-stage amplifier, according to an exemplary embodiment of the present disclosure.

FIG. 1 depicts a multi-stage amplifier 100, according to an exemplary embodiment of the present disclosure. As shown in FIG. 1, the exemplary multi-stage amplifier 100 comprises a plurality of amplification stages 110-1 through 110-N. Each of the amplification stages 110 comprises an amplifying transistor 130 and an active load 140. The amplifying transistors 130 and active loads 140 may be implemented, for example, as n-channel heterojunction field effect transistors or n-channel metal oxide semiconductor field effect transistors. For a more detailed discussion of HJFETs, see, for example, U.S. Pat. Nos. 9,093,548 and 9,748,281; and/or United States Published Patent Application No. 2017/0229588, each incorporated by reference herein in its entirety.

The first amplification stage 110-1 receives a DC bias from an input DC bias circuit 120, and receives an AC input signal through an input capacitor, $C_{IN}$. In one or more embodiments, the AC input signal is a biological signal obtained by capacitive coupling to a biological medium through the input capacitor, $C_{IN}$. The input DC bias circuit 120 may include a passive resistor, $R_{IN}$, as in the embodiment of FIG. 1, or an active load in other embodiments.

In the n-channel embodiment of FIG. 1, the amplification stages 110 have an increasing DC bias level relative to a prior stage. When the amplifying transistors 130 and active loads 140 of each stage 110 are implemented using n-channel devices, the DC bias level will increase for each successive stage 110. In the embodiment of FIG. 1, the DC bias levels increase in equal steps; however, in other embodiments the DC bias levels may not increase (or decrease) in equal steps.

In the embodiment of FIG. 1, an output of a given amplification stage 110-$i$ is directly applied as an input to a subsequent amplification stage 110-$i$+1. In this manner, the traditional capacitive DC blocking employed by conventional techniques, as described above, is not needed in the multi-stage amplifier 100 of FIG. 1.

In one or more embodiments, the amplifying transistors 130 and active loads 140 of each stage 110 are biased in a sub-threshold regime at a $V_{GS}$ equal to approximately the pinch-off voltage (or threshold voltage) of the transistors, as discussed further below in conjunction with FIG. 3. In some embodiments, the amplifying transistors 130 and active loads 140 of each stage 110 have a pinch-off voltage or a threshold voltage of substantially zero volts. As discussed further below in conjunction with FIG. 4, the transistor parameters may be chosen properly during device fabrication to result in a desired pinch-off voltage (or a threshold voltage), e.g., zero volts.

Exemplary values for the drain supply voltage, $V_{dd}$, and number of stages, N, in the multi-stage amplifier 100 are discussed further below in conjunction with FIG. 6.

Consider the following example that employs n-channel HJFET devices with sub-threshold DC bias:

$$V_{bi} \approx E_g/2q + (kT/q)\ln(N_D/n_i)$$

$$V_p \approx V_{bi} - (qN_D/2\varepsilon_{Si})t_{Si}^2$$

$$I_D \approx I_{D0} \exp[q(V_{GS}-V_p)/nkT][1-\exp(-qV_{DS}/kT)]$$

where:
$V_{bi}$: built-in potential of gate heterojunction;
$V_p$: pinch-off voltage of HJFET;
$E_g$: bandgap of crystalline silicon (c-Si) (e.g., LTPS (low-temperature polycrystalline silicon));
$N_D$: c-Si doping;
$n_i$: intrinsic carrier density in c-Si;
$t_{Si}$: c-Si thickness;
k: Boltzmann Constant;
T: absolute temperature;
q: electron charge;
$I_{D0}$: HJFET drain current at $V_{GS}=V_p$ and $V_{DS} \gg kT/q$ (i.e., the thermal voltage, which is 26 mV at room temperature); and
n: ideality factor of gate heterojunction ($1 \leq n \leq 2$).

The transconductance, $g_m$, can be expressed as follows:

$$g_m = \partial I_D/\partial V_{GS} = qI_D/nkT$$

The output resistance, $r_{out}$, can be expressed as follows:

$$r_{out} = (\partial I_D/\partial V_{DS})^{-1} = (kT/qI_D)\exp(qV_{DS}/kT)$$

This example demonstrates a moderately high transconductance, $g_m$, despite a low HJFET drain current, $I_D$. For instance, if $I_D$=50 nA and n=1.3, then $g_m \approx 1.5$ μA/V at room-temperature. In addition, the example demonstrates a high output resistance, $r_{out}$, so far as $V_{DS} \gg kT/q$. For instance, if $I_D$=50 nA and $V_{DS}$=0.25V, then $r_{out} \approx 8$ GΩ, at room-temperature.

Note the above expressions and the derived conclusions are also applicable to MOSFET devices; except that the expression for the HJFET pinch-off voltage ($V_p$) must be replaced with the well-known expression for the MOSFET threshold voltage.

Figure 2:
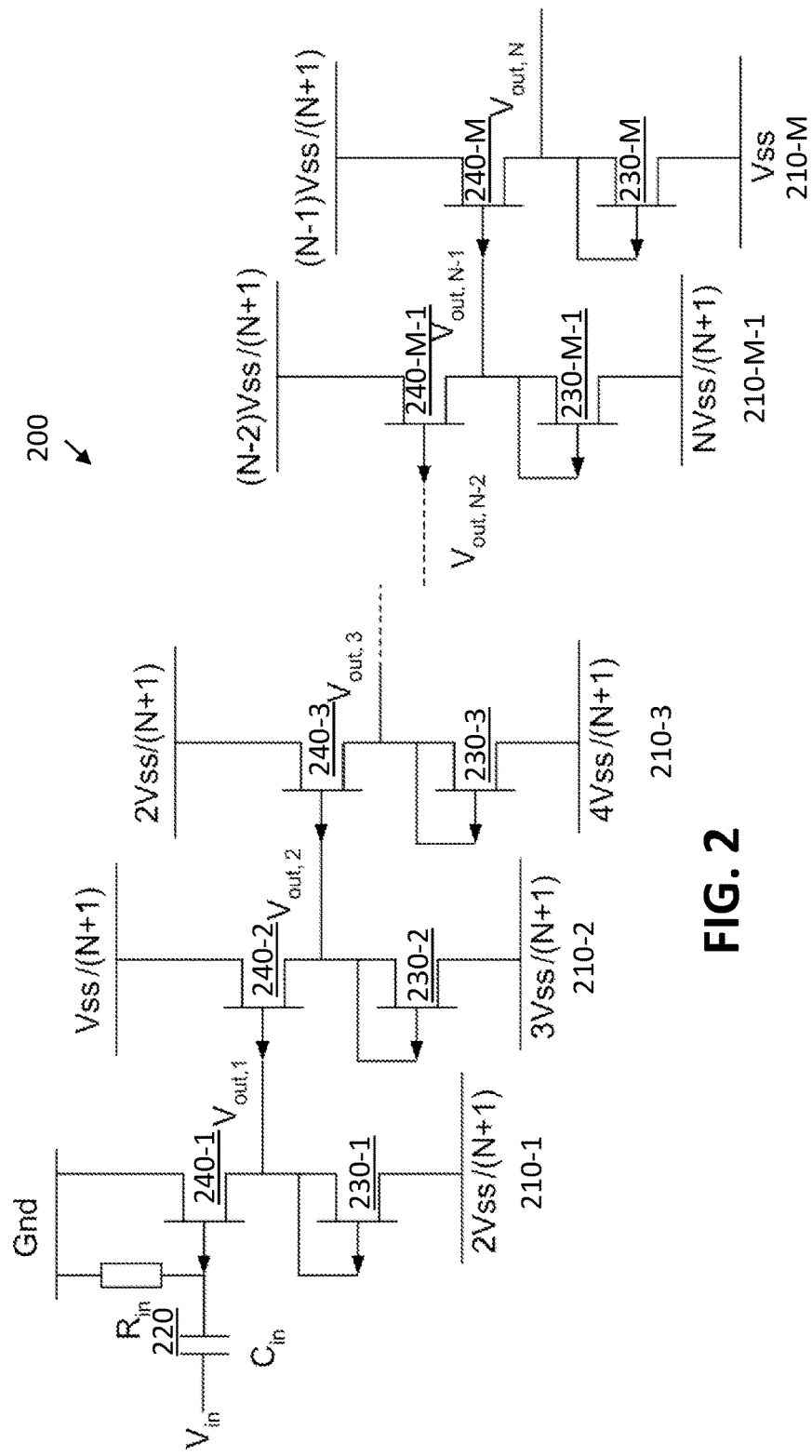
FIG. 2 depicts an alternate implementation of a multi-stage amplifier, according to one embodiment of the present disclosure.

FIG. 2 depicts an alternate implementation of a multi-stage amplifier 200, according to one embodiment of the present disclosure that employs p-channel devices. As shown in FIG. 2, the exemplary multi-stage amplifier 200 comprises a plurality of amplification stages 210-1 through 210-M. Each of the amplification stages 210 comprises an amplifying transistor 230 and an active load 240, in a similar manner as FIG. 1. The amplifying transistors 230 and active loads 240 may again be implemented, for example, as p-channel heterojunction field effect transistors or p-channel metal oxide semiconductor field effect transistors.

The first amplification stage 210-1 receives a DC bias from an input DC bias circuit 220, and receives an AC input signal through an input capacitor, $C_{IN}$, in a similar manner as FIG. 1. In one or more embodiments, the AC input signal is a biological signal obtained by capacitive coupling to a biological medium through the input capacitor, $C_{IN}$. The input DC bias circuit 220 may include a passive resistor or an active load.

In the p-channel embodiment of FIG. 2, the amplification stages 210 have a decreasing DC bias level relative to a prior stage. When the amplifying transistors 230 and active loads 240 of each stage 210 are implemented using p-channel devices, the DC bias level will decrease for each successive stage 210, as would be apparent to a person of ordinary skill in the art. The DC bias levels may or may not decrease in equal steps.

In the embodiment of FIG. 2, an output of a given amplification stage 210-$i$ is directly applied as an input to a subsequent amplification stage 210-$i$+1. In this manner, the traditional capacitive DC blocking employed by conventional techniques, as described above, is not needed in the multi-stage amplifier 200 of FIG. 2.

In one or more embodiments, the amplifying transistors 230 and active loads 240 of each stage 210 are biased in a sub-threshold regime at a $V_{GS}$ approximately equal to the pinch-off voltage or the threshold voltage, as discussed further below in conjunction with FIG. 3. In some embodiments, the amplifying transistors 230 and active loads 240 of each stage 210 have a pinch-off voltage or a threshold voltage of substantially zero volts.

In some embodiments, the amplifying transistors 130, 230 and active loads 140, 240 of each stage 110, 210 (of FIG. 1 or 2) comprise normally-ON transistors. An n-channel JFET (or MOSFET) with a negative pinch-off (or threshold) voltage and a p-channel JFET (or MOSFET) with a positive pinch-off (or threshold) voltage are normally-ON transistors; whereas, an n-channel JFET (or MOSFET) with a positive pinch-off (or threshold) voltage and a p-channel JFET (or MOSFET) with a negative pinch-off (or threshold) voltage are normally-OFF transistors.

Figure 3:
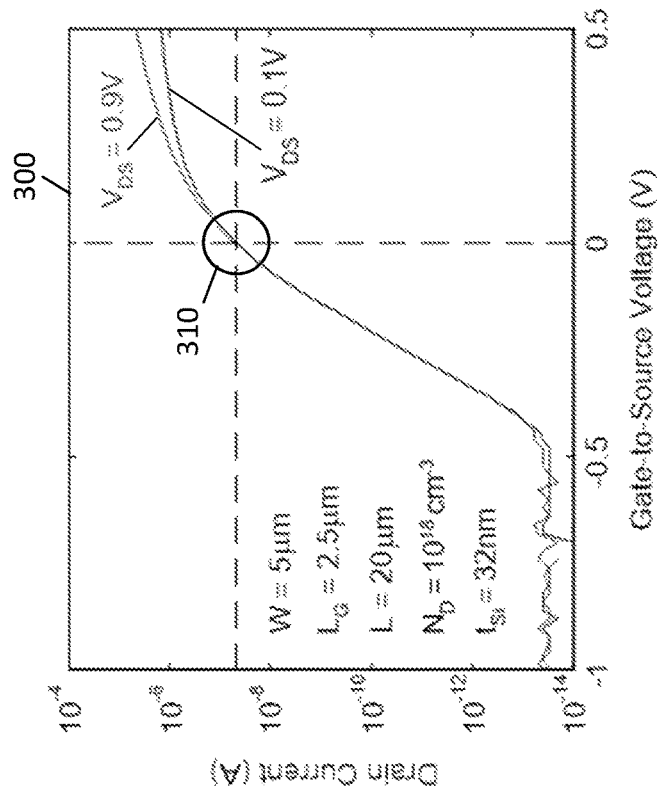
FIG. 3 illustrates a biasing of a transistor based on a drain current as a function of the gate-to-source voltage of the transistor, according to an embodiment of the present disclosure.

FIG. 3 illustrates a biasing of a transistor based on a drain current, $I_D$, as a function of the gate-to-source voltage, $V_{GS}$, of the transistor, according to an embodiment of the present disclosure. The example of FIG. 3 depicts the measured transfer characteristics 300 of an exemplary n-channel HJFET having an underlapped structure for an exemplary drain-to-source voltage of 0.9V and an exemplary drain-to-source voltage of 0.1V. The exemplary HJFET has a channel width (W) of 5 microns, a gate length ($L_G$) of 2.5 microns, a channel length (L) of 20 microns, a doping concentration ($N_D$) of $10^{18}$ cm$^3$, and a c-Si thickness ($t_{Si}$) of 32 nanometers.

As shown in FIG. 3, a substantially best biasing point 310 comprises a point along the transfer curve with a highest slope, i.e., highest derivate of $I_D$ with respect to $V_{GS}$ (therefore resulting in the highest $g_m$ and thus gain) at a substantially lowest drain current (and therefore lowest power consumption). As apparent to those skilled in the art, this substantially best bias point corresponds to the onset of the subthreshold regime and is therefore substantially close to the HJFET pinch-off voltage (or the MOSFET threshold voltage). In the example of FIG. 3, the HJFET has a pinch-off voltage approximately equal to zero. A pinch-off voltage (or threshold voltage) of substantially zero allows biasing an amplifying transistor at the substantially best bias point (e.g., with a $V_{GS}$ of zero) without requiring an additional power supply or a bias circuit (e.g., a resistive voltage divider) that consumes standby power. Moreover, an active load may be implemented by connecting the gate and source of a transistor without requiring a bias voltage between gate and source. As noted above, in one or more embodiments, the amplifying transistors 130, 230 and active loads 140, 240 of each stage 110, 210 (of FIGS. 1 and 2) are biased in a sub-threshold regime at a $V_{GS}$ equal to approximately the pinch-off voltage (or threshold voltage of the transistor), as shown in FIG. 3. In some embodiments, the pinch-off voltage (or threshold voltage) of the amplifying transistors and the active loads is approximately zero volts, which is the case for the HJFET characterized in FIG. 3.

Figure 4:
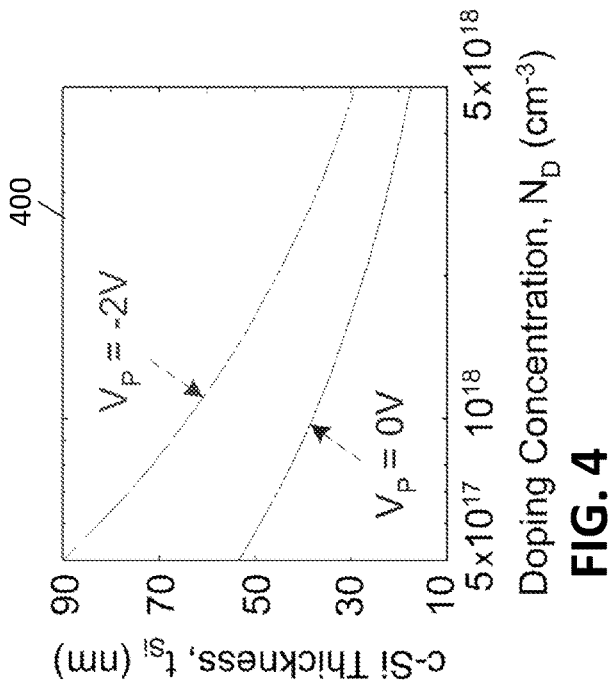
FIG. 4 illustrates a design of a transistor to obtain a desired pinch-off voltage of the transistor based on a crystalline silicon thickness as a function of the doping concentration, and vice versa, according to an exemplary embodiment of the present disclosure.

FIG. 4 illustrates a design of an exemplary HJFET to obtain a desired pinch-off voltage of the transistor by choosing an appropriate combination of a silicon thickness ($t_{Si}$) and a doping concentration ($N_D$), according to an exemplary embodiment of the present disclosure. FIG. 4 illustrates constant pinch-off voltage ($V_p$) contours 400 for a pinch-off voltage of −2V and a pinch-off voltage of 0V. For a given doping concentration, the silicon thickness may be adjusted to obtain a desired pinch-off voltage, e.g., zero volts. Alternatively, for a given silicon thickness, the doping concentration may be adjusted to obtain a desired pinch-off voltage, e.g., zero volts. Similarly, the device parameters of a MOSFET may also be adjusted to obtain a desired threshold voltage, as known in the art. Such device parameters of a MOSFET may include, e.g., the gate dielectric capacitance, the gate electrode work-function and the channel doping concentration.

It is noted that the term "pinch-off" voltage is commonly used for (hetero) junction field effect transistors and the term "threshold voltage" is commonly used for metal oxide field effect transistors. From a circuit design perspective, a pinch-off voltage is essentially the same as threshold voltage.

It is further noted that the HJFET equations provided herein can also be applied for MOSFET devices by replacing the HJFET pinch-off voltage with the MOSFET threshold voltage, as would be apparent to a person of ordinary skill in the art. Moreover, the equations provided for n-channel devices are readily applicable to p-channel devices with minor adjustments to account for the opposite carrier types and voltage polarities, as would be again apparent to a person of ordinary skill in the art.

As noted above, in one or more embodiments, the amplifying transistors 130, 230 and active loads 140, 240 of each stage 110, 210 (of FIGS. 1 and 2) have a pinch-off voltage or a threshold voltage of substantially zero volts.

Figure 5:
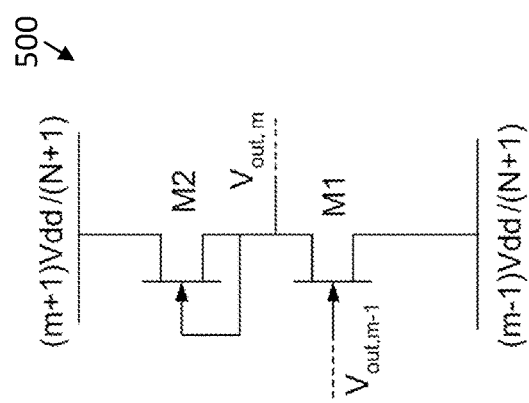
FIG. 5 depicts an exemplary stage of the disclosed multi-stage amplifier, according to one embodiment of the present disclosure.

FIG. 5 depicts an exemplary stage 500 of the disclosed multi-stage amplifiers 100, according to one embodiment of the present disclosure. The stage 500 corresponds to a stage, m, where (1≤m≤N). For a given drain supply voltage, $V_{dd}$, the gain of the multi-stage amplifier 100 may optimized by adjusting a number of stages, N, in the multi-stage amplifier 100.

In one example, a plurality of HJFETs having the same dimensions are biased in the sub-threshold regime and the bias levels of the amplifier stages increase in equal voltage steps, as illustrated in the embodiment of FIG. 1. Referring to an m-th stage 500 of the exemplary multi-stage amplifier, assuming that $V_{dd} \gg (N+1) kT/q$ the drain current of M1 ($I_{D1}$), the drain current of M2 ($I_{D2}$), the transconductance of M1 ($g_m$), the output resistance of M1 ($r_{out1}$) and the output resistance of M2 ($r_{out2}$) are given by:

$$I_{D1}=I_{D2}=I_{D0}\exp[q(V_{GS}-V_P)/nkT]=I_D$$

$$g_{m1}=qI_D/nkT$$

$$r_{out1}=r_{out2}=(kT/qI_D)\exp[qV_{dd}/(N+1)kT]$$

Therefore, the voltage gain of the m-th stage ($A_{V,m}$) is given by:

$$A_{V,m} = V_{out,m}/V_{out,m-1} = \\ -g_{m1}(r_{out1}\|r_{out2}) = -g_{m1}r_{out1}/2 = (1/2n)\exp[qV_{dd}/(N+1)kT]$$

The voltage gain of the multi-stage amplifier ($A_V$) is the product of the voltage gains of the N stages and given by:

$$A_V=V_{out,N}/V_{in}=(A_{V,m})^N=(1/2n)^N\exp[qV_{dd}N/(N+1)kT]$$

The optimum N (which results in maximum $A_V$) may be obtained by calculating the derivate of $A_V$ (or equivalently the derivative of the natural logarithm of $A_V$) with respect to N, and equating the result to zero, as follows:

$$\ln A_V=-N\ln(2n)+N/(N+1)(qV_{dd}/kT)$$

$$\partial(\ln A_V)/\partial N=-\ln(2n)+(qV/kT)/(N+1)^2=0$$

The optimum N obtained from solving the above equation is given by:

$$N_{opt} = \left(\frac{qV_{dd}}{kT\ln 2n}\right)^{1/2} - 1.$$

therefore the optimum number of stages is an integer close to $N_{opt}$.

Figure 6:
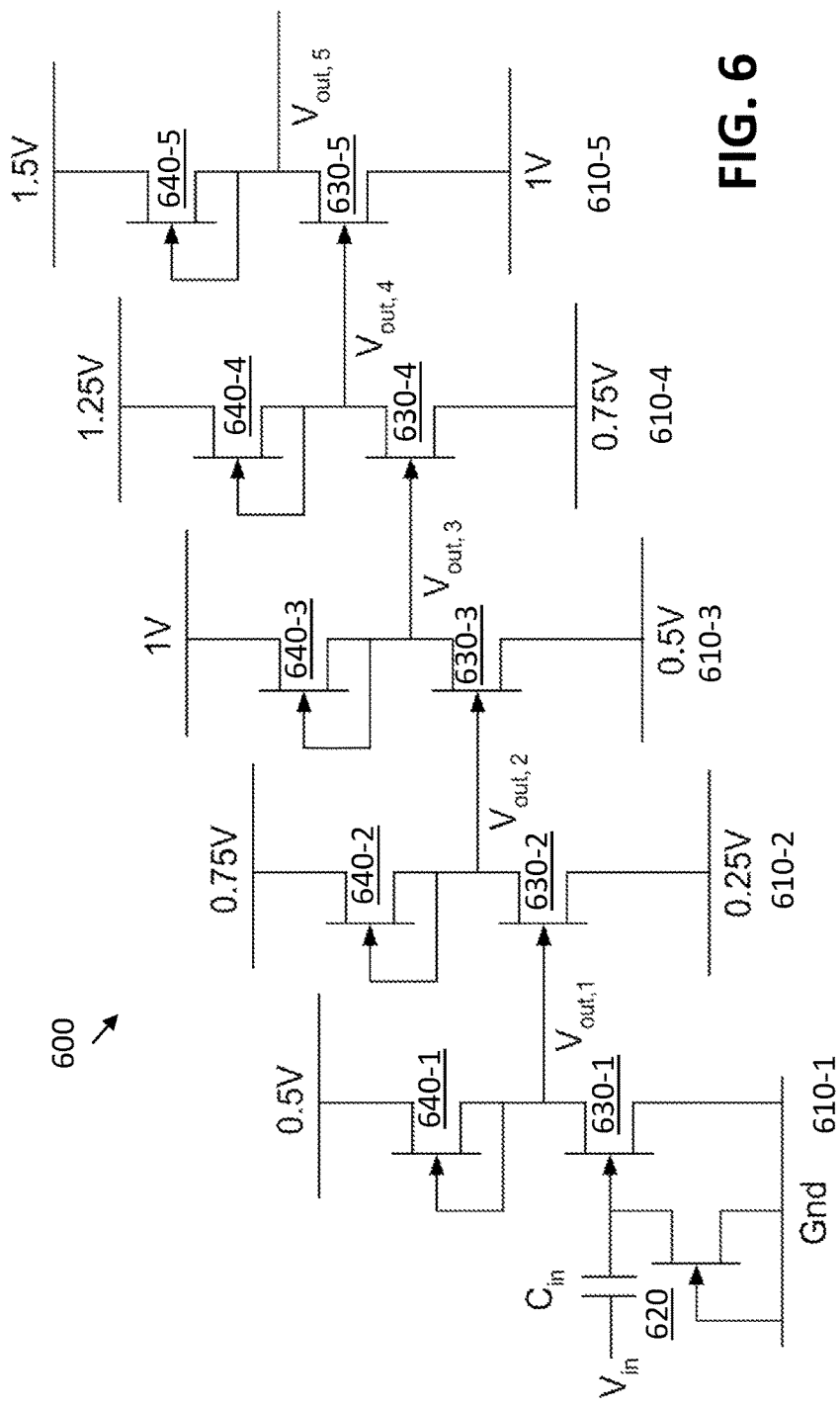
FIG. 6 illustrates an exemplary implementation of the multi-stage amplifier of FIG. 1, according to an exemplary embodiment of the present disclosure.

FIG. 6 illustrates an exemplary implementation 600 of the multi-stage amplifier 100 of FIG. 1, according to an exemplary embodiment of the present disclosure. As shown in FIG. 6, the exemplary multi-stage amplifier 600 comprises a plurality of amplification stages 610-1 through 610-5. Each of the amplification stages 610 comprises an amplifying transistor 630 and an active load 640. The amplifying transistors 630 and active loads 640 may be implemented, for example, as n-channel heterojunction field effect transistors or n-channel metal oxide semiconductor field effect transistors.

The first amplification stage 610-1 receives a DC bias from an input DC bias circuit 620, and receives an AC input signal through an input capacitor, $C_{IN}$. In one or more embodiments, the AC input signal is a biological signal obtained by capacitive coupling to a biological medium through the input capacitor, $C_{IN}$. In the illustrated embodiment, the input DC bias circuit 620 comprises an active load.

In the example of FIG. 6, the amplifying transistors 630 and active loads 640 are comprised of n-channel heterojunction field-effect transistors having transfer characteristics as depicted in FIG. 3. The drain supply voltage, $V_{dd}$, is equal to 1.5 volts, and the number of stages is five. The optimum number of stages, $N_{opt}$, computed in the manner described above, is in the range of 5.4 to 8.1 (for n=2 to 1); for n=1.2, $N_{opt}$ is equal to 7.1

It is noted that if 7 stages are used (N=7), $V_{DS}=V_{dd}/(N+1)=0.188V$ which is ~7kT/q at room temperature. Typically, ~5kT/q is sufficient to ensure saturation in the subthreshold regime; however, to increase the design margin, N=5 was used and $V_{DS}=0.25V\approx10kT/q$ at room-temperature. It is further noted that at 125° C., 0.188V≈5kT/q, whereas 0.25V≈7kT/q, which provides a wider voltage margin for saturation.

It is also noted that an HJFET was used as the input resistor (e.g., in the form of an active load). If the amplitude of the input signal is much lower than kT/q (amp($V_{in}$)=1 μV in this example), $I_D=I_{D0}[1-\exp(-qV_{ds}/kT)]\approx I_{D0}qV_{ds}/kT$ for this HJFET; equivalent to a linear resistor. Alternatively, ohmic resistors (elements) comprised of a-Si, poly-Si, etc. may be used.

For an input signal having an amplitude of 1 μV; the amplitude of the output signal is approximately 100 mV, as determined by circuit simulation using HJFET device parameters extracted from the measurement of the fabricated devices. Thus, the gain of this exemplary amplifier is approximately 100,000. Each stage consumes less than 50 nA of standby current.

In the previous example of FIG. 6, standby (DC) power consumption is given by $2I_{D0}V_{dd}N/(N+1)$, which is a slowly increasing function of N (asymptotizing to $2I_{D0}V_{dd}$).

In one or more embodiments, the resistance of the input bias network, $R_{in}$, must be small enough to generate thermal noise $(4kTR_{in})^{1/2}$ sufficiently smaller than that of the input signal (e.g., ~0.1 μV for 500 KΩ at room temperature). The product of the input resistance and the input capacitance of the input bias network, $R_{in}\times C_{in}$, must be large enough to allow sufficiently low frequencies of interest (e.g., note cut-off frequency≈$1/2\pi R_{in}C_{in}$).

In some embodiments, the HJFETs may be biased in saturation above pinch-off; however, these embodiments may exhibit lower gain and/or higher power consumption compared to embodiments using subthreshold operation. Similarly, MOSFETs may be biased in saturation above threshold, in some embodiments.

Figure 7:
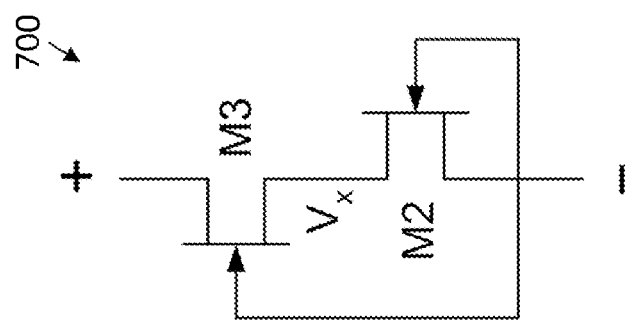
FIG. 7 depicts an active load portion of an exemplary stage of the disclosed multi-stage amplifier, according to one embodiment of the present disclosure.

In one or more embodiments, the HJFET pinch-off voltage may be negative and in order to bias the HJFET in the sub-threshold regime without requiring additional negative bias supply for the gate, an HJFET pair may be used as shown in FIG. 7. FIG. 7 depicts an active load portion of an exemplary stage 700 of the disclosed multi-stage amplifier, according to one embodiment of the present disclosure. In the embodiment of FIG. 7, the gate-to-source voltage of transistor M2 is zero ($V_{GS, M2}=0$) and given that the pinch-off voltage is negative, it is biased in the linear regime above the pinch-off voltage. However, because of the voltage drop across transistor M2, the gate-to-source voltage of transistor M3 is negative ($V_{GS, M3}<0$). Depending on whether $V_{GS,M3}$ is more or less negative than the pinch-off voltage, transistor M3 operates below or above pinch-off, respectively. This can be determined by solving the HJFET current-voltage equations below. Transistor M3 is biased in the sub-threshold regime (below pinch-off) if equation (1) has a solution and in the saturation regime (above pinch-off) if equation (2) has a solution:

$$I_{D0,M3}\exp\left(-\frac{qV_x}{nkT}\right) = G_{0,M2}|V_p|\left[\frac{V_x}{|V_p|} - \frac{2}{3}\left(\frac{V_x}{|V_p|}\right)^{3/2}\right] \quad (1)$$

$$G_{0,M3}|V_p|\left[\frac{-V_x}{|V_p|} + \frac{2}{3}\left(\frac{V_x}{|V_p|}\right)^{3/2} + \frac{1}{3}\right] = G_{0,M2}|V_p|\left[\frac{V_x}{|V_p|} - \frac{2}{3}\left(\frac{V_x}{|V_p|}\right)^{3/2}\right] \quad (2)$$

$$I_{D0} = (W/L)(2\pi\varepsilon_{si}kT/qN_D)^{1/2}\exp(q|V_p|/nkT)$$

$$G_0 = (W/L)qN_D\mu_n t_{si}$$

where $\mu_n$ is the electron mobility and the remaining parameters were defined above. In the case of MOSFET devices, the same approach may be used to determine the operation regime of M3 using the well-known MOSFET equations for the linear and saturation regimes above threshold.

It is to be understood that the terms "about," "approximately," or "substantially" as used herein with regard to thicknesses, widths, percentages, ranges, etc., are meant to denote being close or approximate to, but not exactly. For example, the term "about" or "substantially" as used herein implies that a small margin of error is present such as, by way of example only, 2% or less than the stated amount.

Embodiments of the disclosure as shown in FIGS. 1, 2 and 6 may be implemented in the form of integrated circuits. In an integrated circuit implementation, identical dies are typically formed in a repeated pattern on a surface of a semiconductor wafer or a semiconductor substrate layer (also known as a base layer) disposed on an insulating carrier substrate (also known as a handle substrate) such as glass or plastic. Each die includes one or more circuit cores and circuitry as described herein, and may include other structures or circuits. The individual die are cut or diced from the wafer, and then each die is packaged as an integrated circuit. One skilled in the art would know how to dice wafers and package die to produce integrated circuits. Integrated circuits so manufactured are considered embodiments of this disclosure. Moreover, embodiments of the disclosure as shown in FIGS. 1, 2 and 6 can be implemented in the form of integrated circuits of a system-on-chip.

A multi-stage amplifier, such as shown in FIGS. 1, 2 and 6, can be implemented in a wide range of applications and state of the art technologies in which amplification of low-amplitude and low-frequency signals is required. An integrated circuit in accordance with the present disclosure can be employed in any application and/or electronic system. Systems incorporating such integrated circuits are considered part of this disclosure. Given the teachings of the disclosure provided herein, one of ordinary skill in the art will be able to contemplate other implementations and applications of the techniques of the disclosure.

In this regard, although embodiments of the disclosure have been described herein with reference to the accompanying drawings, it is to be understood that embodiments of the disclosure are not limited to the described embodiments, and that various changes and modifications may be made by one skilled in the art resulting in other embodiments of the disclosure within the scope of the following claims.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A multi-stage amplifier, comprising:
a plurality of amplification stages, wherein each of said amplification stages comprises an amplifying transistor and an active load, wherein each of said amplification stages has one of an increasing DC bias level and a decreasing DC bias level relative to a prior stage, and wherein an output of a given one of said amplification stages is directly applied as an input to a subsequent one of said amplification stages.

2. The multi-stage amplifier of claim 1, wherein one or more of said amplifying transistors and said active loads are biased in a sub-threshold regime.

3. The multi-stage amplifier of claim 1, wherein one or more of said amplifying transistors and said active loads comprise normally-ON transistors.

4. The multi-stage amplifier of claim 1, wherein one or more of said amplifying transistors and said active loads comprise heterojunction field effect transistors.

5. The multi-stage amplifier of claim 1, wherein one or more of said amplifying transistors and said active loads have a pinch-off voltage or a threshold voltage of substantially zero volts.

6. The multi-stage amplifier of claim 1, wherein a first one of said amplification stages receives a DC bias from an input DC bias circuit, and receives an AC input signal through an input capacitor.

7. The multi-stage amplifier of claim 6, wherein the AC input signal is a bio-electric signal obtained by capacitive coupling to a biological medium through the input capacitor.

8. The multi-stage amplifier of claim 6, wherein the input DC bias circuit comprises an active load.

9. The multi-stage amplifier of claim 1, wherein a gain of said multi-stage amplifier is determined based on a number of said amplification stages for a given drain supply voltage.

10. A method for amplifying a signal, comprising:
obtaining said signal; and
applying said signal to a multi-stage amplifier, wherein said multi-stage amplifier comprises a plurality of amplification stages, wherein each of said amplification stages comprises an amplifying transistor and an active load, wherein each of said amplification stages has one of an increasing DC bias level and a decreasing DC bias level relative to a prior stage, and wherein an output of a given one of said amplification stages is directly applied as an input to a subsequent one of said amplification stages.

11. The method of claim 10, further comprising determining a gain of said multi-stage amplifier based on a number of said amplification stages for a given drain supply voltage.

12. The method of claim 10, wherein one or more of said amplifying transistors and said active loads comprise heterojunction field effect transistors.

13. The method of claim 10, wherein one or more of said amplifying transistors and said active loads are biased in a sub-threshold regime.

14. The method of claim 10, wherein one or more of said amplifying transistors and said active loads are comprised of normally-ON transistors.

15. The method of claim 10, wherein one or more of said amplifying transistors and said active loads have a pinch-off voltage or a threshold voltage of substantially zero volts.

16. The method of claim 10, further comprising providing an input DC bias and an input AC signal to a first one of said amplification stages, wherein the input DC bias is generated using an input DC bias circuit and the AC input signal is obtained by capacitive coupling to a biological medium using an input capacitor.

17. An integrated circuit, comprising:
a multi-stage amplifier, comprising a plurality of amplification stages, wherein each of said amplification stages comprises an amplifying transistor and an active load, wherein each of said amplification stages has one of an increasing DC bias level and a decreasing DC bias level relative to a prior stage, and wherein an output of a given one of said amplification stages is directly applied as an input to a subsequent one of said amplification stages.

18. The integrated circuit of claim 17, wherein one or more of said amplifying transistors and said active loads comprise heterojunction field effect transistors.

19. The integrated circuit of claim 18, wherein the heterojunction field effect transistors are comprised of low-temperature polysilicon.

20. The multi-stage amplifier of claim 1, wherein the multi-stage amplifier is a voltage amplifier having a gain greater than 1.

* * * * *